United States Patent [19]
Thierman

[11] Patent Number: 5,303,024
[45] Date of Patent: Apr. 12, 1994

[54] SCINTILLOMETER FOR THE MEASURMENT OF THE STRUCTURE FUNCTION CONSTANT AND THE INNER SCALE OF ATMOSPHERIC REFRACTIVE INDEX FLUCTUATIONS

[76] Inventor: Volker Thierman, Panoramastrasse 67, D-7406 Mossingen 5, Fed. Rep. of Germany

[21] Appl. No.: 864,856

[22] Filed: Apr. 7, 1992

[30] Foreign Application Priority Data

Apr. 24, 1991 [DE] Fed. Rep. of Germany ....... 4113308

[51] Int. Cl.$^5$ ............................ G01N 21/41; G01J 4/00
[52] U.S. Cl. .................................... 356/128; 356/365; 250/225
[58] Field of Search .............. 356/128, 129, 130, 336, 356/338, 364, 365, 370, 435–438, 351, 361; 250/225, 573, 338.1, 338.5

[56] References Cited

U.S. PATENT DOCUMENTS

| | | | |
|---|---|---|---|
| 4,099,878 | 7/1978 | Lee ........................................ | 356/128 |
| 4,613,938 | 9/1986 | Hansen et al. ........................ | 356/338 |
| 5,037,202 | 8/1991 | Batchelder et al. ................. | 356/364 |
| 5,150,171 | 9/1992 | Hill et al. ............................. | 356/128 |

FOREIGN PATENT DOCUMENTS

3902015C2  1/1989  Fed. Rep. of Germany .

OTHER PUBLICATIONS

P. M. Livingston, Applied Optics 11 (1972), p. 684.
G. R. Ochs and R. J. Hill, Applied Optics 24 (1985), p. 2430.
E. Azoulay, V. Thiermann, A. Jetter, A. Kohnle, Z. Azar, Journal of Physics D S21 (1988), p. 21.
R. G. Frehlich, Applied Optics 27 (1988), p. 2194.

Primary Examiner—Richard A. Rosenberger
Assistant Examiner—Hoa Q. Pham
Attorney, Agent, or Firm—Carter & Schneider

[57] ABSTRACT

There is provided a scintillometer for the measurement of the structure function constant and the inner scale of atmospheric refractive index fluctuations including a transmitter unit with a source emitting radiation. Included in the transmitter unit is a piece of birefringent material which splits the radiation into two displaced orthogonally polarized components. A receiver unit which substantially contains two detectors receives the two components of the radiation. The detectors are combined with polarizers in such a way that at least one detector has a preferred sensitivity to one polarization component and the apparent distance of the detectors in the plane perpendicular to the propagation direction approximately equals the beam displacement produced at the transmitter.

14 Claims, 2 Drawing Sheets

SCINTILLOMETER FOR THE MEASURMENT OF THE STRUCTURE FUNCTION CONSTANT AND THE INNER SCALE OF ATMOSPHERIC REFRACTIVE INDEX FLUCTUATIONS

BACKGROUND OF THE INVENTION

Scintillation denotes the apparent temporal variation of the intensity of a remote radiation source. This effect is well known from star light twinkling. Physically scintillation may be defined as the variance of the intensity received at a detector. Instruments which measure scintillation are called scintillometers. Scintillometers generally consist of a transmitter and a receiver unit. The transmitter contains a source which emits radiation usually in the visible or infrared. At the receiver the intensity fluctuations are measured. The distance between transmitter and receiver typically is a few ten to a few hundred meters.

For such wavelengths and scales the scintillation magnitude, i.e. the variance of the intensity, is determined by the structure function constant $C_n^2$ and the inner scale $l_0$ of the turbulent refractive index fluctuations of the air. $C_n^2$ is a measure of the amplitude of the refractive index fluctuations and $l_0$ defines the smallest occuring turbulence eddies. The mathematics of this relationship is well known.

Scintillometers may be used to determine $C_n^2$ and $l_0$. An important application of scintillometers is the determination of the turbulent fluxes of heat and momentum in the lowest atmosphere (V. Thiermann and H. Grassl, Boundary-Layer Meteorology 58 (1992), pp. 367). The advantages of using scintillation for turbulence measurements are the high accuracy, the averaging over the optical propagation path, and the purely optical, contact-free access.

In order to derive the two quantities $C_n^2$ and $l_0$ from scintillation measurements, two independent informations must be available. So far the following methods have been proposed:

1. the simultaneous measurement of scintillation variances over two differently long propagation paths (P. M. Livingston, Applied Optics 11 (1972), pp. 684),
2. the simultaneous measurement of scintillation variances of a coherent and an incoherent source (G. R. Ochs and R. J. Hill, Applied Optics 24 (1985), pp. 2430),
3. the simultaneous measurement of scintillation variances and covariances at two different wavelengths (E. Azoulay, V. Thiermann, A. Jetter, A. Kohnle, Z. Azar, Journal of Physics D S21 (1988), pp. 21),
4. the simultaneous measurement of scintillation variances and covariances at displaced detectors. Here the radiation is emitted from a single source (R. G. Frehlich, Applied Optics 27 (1988), pp. 2194).

Method 1 has the disadvantage that it compares scintillation over different paths where the turbulence is not necessarily the same. It thus requires spatial homogeneity of the turbulence field, otherwise errors will result. The methods 2 and 3 have the disadvantage that they need either two different wavelengths or a coherent and an incoherent source. The realization of such systems requires much technical effort.

Method 4 compares the covariance at at least two displaced detectors with the variance at a single detector. The detectors are illuminated by the same source. This method is technically simple. However, the spatial weighting functions for the variances and covariances are very different. The spatial weighting functions describe the contribution the different positions along the propagation path make to the measured variances or covariances. The weighting function of the variance is symmetric with its peak at the path center. The weighting function of the covariance is asymmetric with its peak close to the transmitter. If the variances and covariances are compared, turbulence statistics originating from different locations are compared and, as with method 1, inhomogeneities of the turbulence field may cause severe errors.

OBJECT OF THE INVENTION

It is therefore the object of the invention to provide a system which at the same time is technically simple and avoids the error source that statistical quantities originating from different path positions are compared.

SUMMARY OF THE INVENTION

The invention is a scintillometer where in the transmitter unit a source emits radiation preferably in the visible or infrared which then passes through a birefringent material, splitting the beam into two displaced components with orthogonal polarization, thus creating two virtual sources of a different polarization, and where in the receiver unit the intensity of the radiation originating from each of the two virtual sources is measured at two displaced detectors, the components of the radiation being identified by polarizers. The polarizing component may be a polarizing beam splitter. The apparent distance of the centers of the detectors in the receiver plane substantially equals the displacement caused by the birefringent material in the transmitter unit. The variances and covariances of the intensity are used to calculate the structure function constant and the inner scale of refractive index fluctuations. Due to the fact that the separation of the virtual sources equals the apparent distance of the receivers, a quite similar weighting function is achieved for the variances and the covariances.

BRIEF DESCRIPTION OF THE DRAWINGS

The subject matter which is regarded as the invention is set forth in the appended claims. The invention itself, however, may be better understood with reference to the following description taken in conjunction with the accompanying drawings in which:

DESCRIPTION OF THE PREFERRED EMBODIMENTS

Before going into details of the embodiment, some restrictions concerning the instrumental dimensions and source properties shall be discussed. In order to obtain sensitivity to the inner scale $l_0$ of refractive index fluctuations the radiating aperture of the source as well as the apertures of the detectors must be small compared to $l_0$. Since $l_0$ measures several millimeters, aperture sizes must be less than a few millimeters. Because the Fresnel zone radius, i.e. the square root of the product of optical propagation path length and wavelength, must approximately equal the inner scale, propagation path lengths in the order of 100 m are needed. To obtain a sufficiently high radiation intensity at the detector, a source with a small aperture, a small divergence and a sufficiently high output power is required.

Appropriate sources are lasers in particular. The embodiment of FIG. 1 uses a laser diode (1), which is small in size and economic in power consumption, has a long lifetime and can easily be modulated. In order to reduce the divergence of the beam, a collimator (2) follows. A homogeneous illumination in the receiver plane is achieved by special filtering of the beam. This is especially necessary for laser diodes, which do not have ideal wave front properties. Spatial filtering is performed by letting the radiation pass a pinhole (3) in the focus of the collimator (2). Laser diode (1), collimator (2) and pinhole (3) form the radiation source. However the invention is independent of the type of the source. For example, a laser without any further optics may be used, if its output power, divergence, and coherence quality suffices. The source may emit a continuous wave or a wave modulated in amplitude, phase or frequency. Modulation has the advantage that the signal can later be separated from background radiation. Amplitude modulation is easiest to apply.

Figure 1:
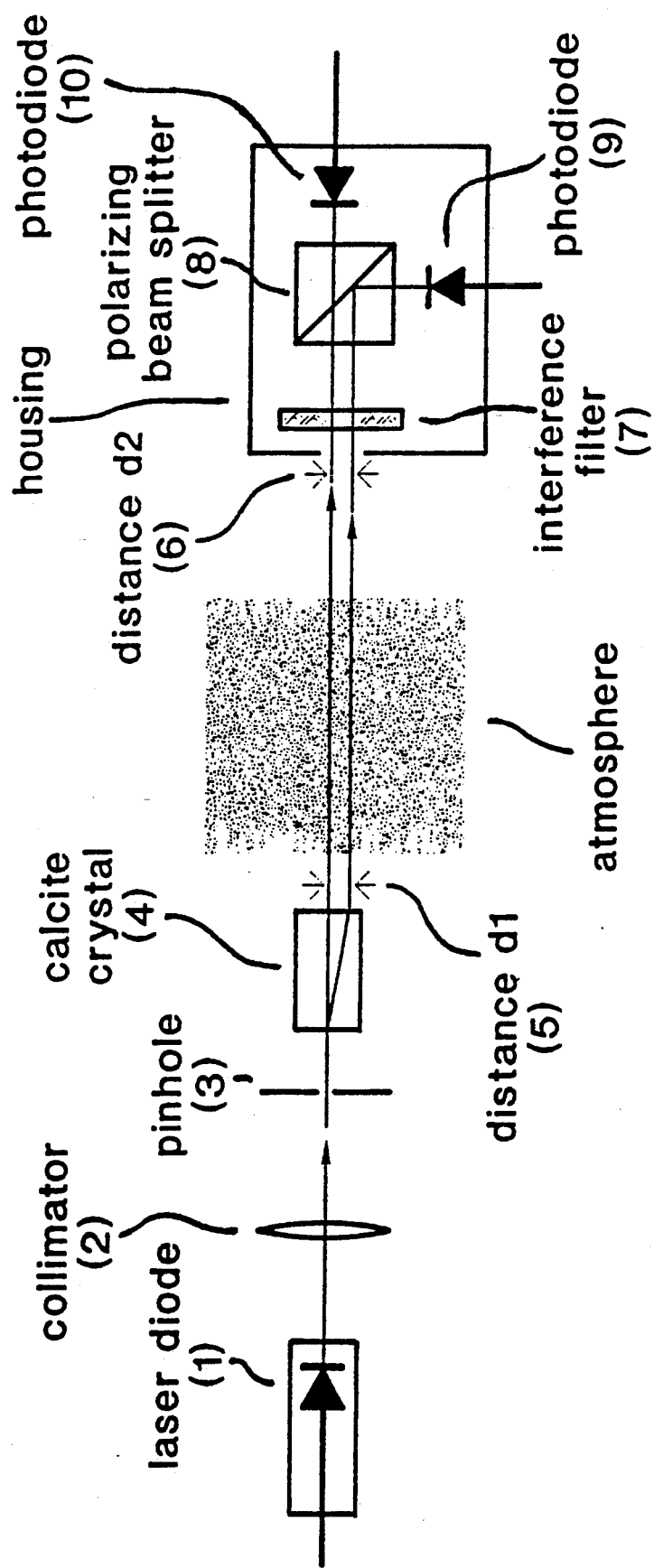
FIG. 1 is a schematic of one possible realization of the invention; and, as an example calculated for typical instrumental dimensions, there are given in FIG. 2: the relative path weighting functions for the intensity, in FIG. 3: the relative path weighting functions for the intensity covariances, and in FIG. 4: the dependence of the inner scale on the intensity correlation coefficient.

Before the beam leaves the transmitter unit, it passes through a birefringent material. In the embodiment of FIG. 1 this material is a calcite crystal (4). The crystal produces two orthogonally polarized beams with a displacement d1 (5). The optimum displacement d1 depends on the wavelength, the propagation path length and the size of the $l_0$ values to be measured; d1 is in the order of a few millimeters. For an atmospheric path of 100 m length a displacement of 2.7 mm is suitable.

After the two beams have left the transmitter they diverge and therefore overlap. The divergence is at least that of a diffraction limited beam for the given radiating aperture. For applicability of the theory it is required that at the propagation path center the beam diameter measures at least several Fresnel zones. Larger divergences have the disadvantage to reduce the radiation intensity at the receiver. Typical divergences are several milliradians.

Because of the small beam divergences both beams must be very parallel. The invention ensures very parallel beams by the fact that in the transmitter both beams originate from the same source and the birefringent crystal only creates a parallel displacement. Note that in FIG. 1 the two straight lines indicating the light path do not strictly stand for the axes following the beam centers but connect the centers of the two beams at the transmitter with the centers of the photosensitive areas of the respective detectors.

At the entrance of the receiver unit, a small aperture and an interference filter (7), which is transparent in the range of the used wavelength, reduces the background radiation. If the radiation of the source is not modulated, the background radiation must be eliminated to avoid contributions of background radiation to the measured intensity variations. If the radiation of the source is modulated, the reduction of background radiation improves the signal-to-noise ratio.

In the embodiment of FIG. 1, a polarizing beam splitter (8) separates the differently polarized components. Two photodiodes (9, 10) are positioned that each of them receives its signal from one source only and the apparent distance d2 (6) of the centers of their photosensitive areas equal the beam displacement d1 (5) at the transmitter. The apparent distance is the distance the detectors appear to have vertical to the viewing direction if seen from the transmitter position.

There are also other embodiments possible than that shown in FIG. 1. For example, if the spatial dimensions of the detectors permit, they can be positioned side by side with a polarizing filter in front of each of them. Another realization may use light conducting wires to transmit the light to remote detectors. In all cases the apparent distance of the detector centers must equal d1.

If the polarization in the receiver unit is not perfect, one or both detectors observe radiation not only from one but, to a certain fraction, also from the other virtual source. If these fractions are known, this effect can mathematically be corrected for in the data evaluation. Note that the invention utilizes the fact that depolarization of the radiation by turbulent refractive index fluctuations is negligible.

The advantage of the invention compared to a system where simply a single source illuminates two detectors is given by the fact that in a technically very simple way similar spatial weighting functions of the measured variances and covariances are now achieved. The weighting functions can mathematically be calculated; it can intuitively be understood by the reciprocity theorem of light that the covariances have a symmetric shape if the displacement of the sources equals the displacement of the detectors.

Figure 2:
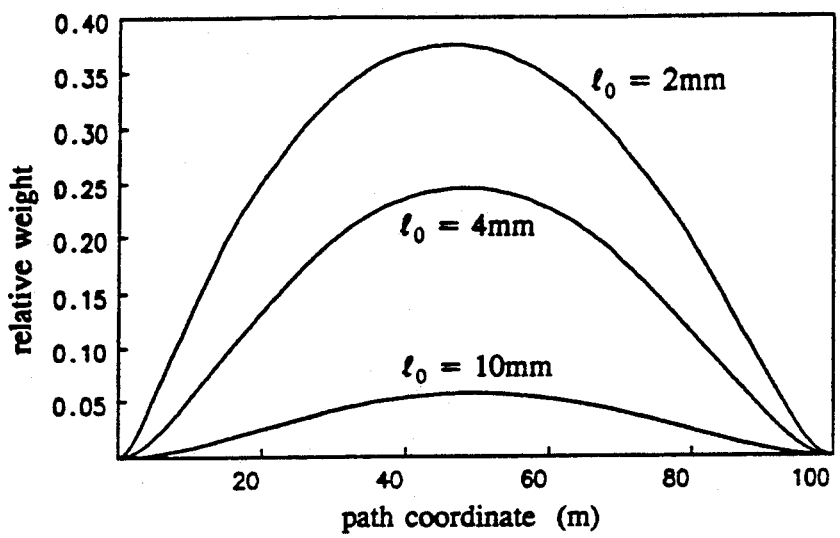
Figure 3:
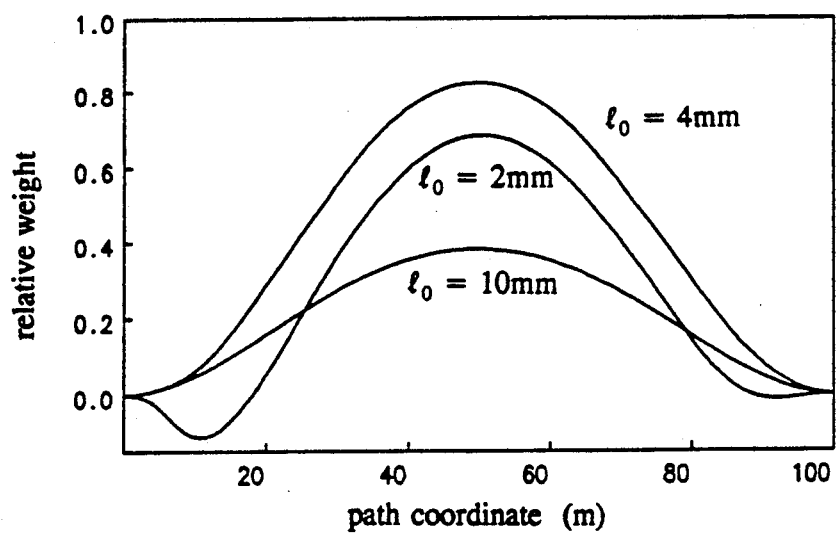

The FIGS. 2 and 3 give examples of calculated weighting functions of the variances and covariances for a path length of 100 m, a wavelength of 670 nm, a beam displacement of 2.7 mm, virtual point sources, detector diameters of 2.5 mm and $l_0$ values of 2 mm, 4 mm and 10 mm. These Figures demonstrate that, apart from a not relevant factor, all weighting functions are quite similar. Some remaining asymmetrics are caused by the non-zero detector diameters in this example.

The further evaluation of the data can be summarized as follows. The variance is proportional to $C_n^2$ and also is a known function of $l_0$. The ratio of the covariance and the variance is the correlation coefficient. The correlation coefficient is a function of $l_0$ only.

Figure 4:
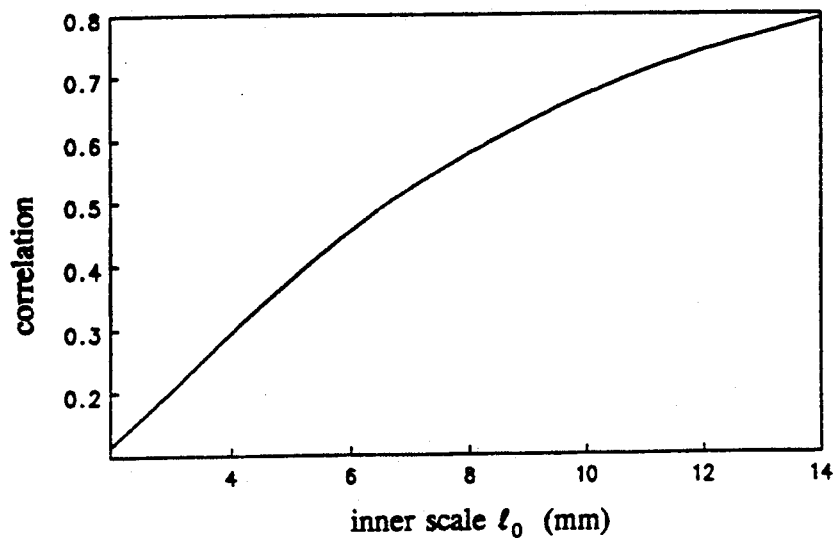

For the configuration used in the calculation of FIGS. 2 and 3 this dependence is given in FIG. 4. Hence the measured correlation coefficient directly provides $l_O$. Once $l_O$ is known, $C_n^2$ follows from the single detector variances.

I claim:

1. A scintillometer for the measurement of the structure function constant and the inner scale of atmospheric refractive index fluctuations comprising:
   a transmitter unit with a single source emitting radiation;
   said transmitter unit formed by a piece of birefringent material which splits the radiation into two displaced and orthogonally polarized divergent beams;
   a receiver unit; a line of sight between said transmitter unit and said receiver unit; atmospheric media situated along said line of sight; said divergent beams passing through said atmospheric media; said receiver unit containing two detectors; at least one detector having a preferred sensitivity to one polarization component; the apparent location of said detectors substantially being in a plane perpendicular to said line of sight; the apparent distance between the detectors in said plane substantially equals the beam displacement produced at said transmitter.

2. A scintillometer as set forth in claim 1 wherein said source is a laser.

3. A scintillometer as set forth in claim 2 wherein the beams divergence in said transmitter unit is altered by an optical collimator.

4. A scintillometer as set forth in claim 3 wherein said radiation is amplitude, phase or frequency modulated; said detectors emitting signals; said signals being demodulated.

5. A scintillometer as set forth in claim 4 further including a spatial filter forming a part of said transmitter unit for improving said beams coherence.

6. A scintillometer as set forth in claim 3 further including a spatial filter forming a part of said transmitter unit for improving said beams coherence.

7. A scintillometer as set forth in claim 2 wherein said radiation is amplitude, phase or frequency modulated; said detectors emitting signals; said signals being demodulated.

8. A scintillometer as set forth in claim 2 wherein said laser is a semiconductor.

9. A scintillometer as set forth in claim 1 wherein the beams divergence in said transmitter unit is altered by an optical collimator.

10. A scintillometer as set forth in claim 9 wherein said radiation is amplitude, phase or frequency modulated; said detectors emitting signals; said signals being demodulated.

11. A scintillometer as set forth in claim 10 further including a spatial filter forming a part of said transmitter unit for improving said beams coherence.

12. A scintillometer as set forth in claim 9 further including a spatial filter forming a part of said transmitter unit for improving said beams coherence.

13. A scintillometer as set forth in claim 1 wherein said radiation is amplitude, phase or frequency modulated; said detectors emitting signals; said signals being demodulated.

14. A scintillometer for the measurement of the structure function constant and the inner scale of atmospheric refractive index fluctuations comprising:

a transmitter unit with a single laser emitting radiation; said transmitter unit formed by a piece of birefringent material which splits the radiation into two displaced and orthogonally polarized divergent beams; said beams divergence in said transmitter unit being altered by an optical collimator; said radiation being amplitude, phase or frequency modulated;

a receiver unit;

a line of sight between said transmitter unit and said receiver unit;

atmospheric media situated along said line of sight; said divergence beams passing through said atmospheric media; said receiver unit containing two detectors; at least one detector having a preferred sensitivity to one polarization component; the apparent location of said detectors being in a plane perpendicular to said line of sight; the apparent distance between the detectors in said plane substantially equals of the beam displacement produced at said transmitter;

a spatial filter forming a part of said transmitter unit for improving said beams coherence.

* * * * *